US008366610B2

(12) United States Patent
Matsui

(10) Patent No.: US 8,366,610 B2
(45) Date of Patent: Feb. 5, 2013

(54) ENDOSCOPE APPARATUS

(75) Inventor: Koichi Matsui, Koganei (JP)

(73) Assignee: Olympus Corporation, Tokyo (JP)

( * ) Notice: Subject to any disclaimer, the term of this patent is extended or adjusted under 35 U.S.C. 154(b) by 1376 days.

(21) Appl. No.: 12/012,575

(22) Filed: Feb. 4, 2008

(65) Prior Publication Data

US 2009/0284588 A1 Nov. 19, 2009

(30) Foreign Application Priority Data

Feb. 5, 2007 (JP) ................................. 2007-025983

(51) Int. Cl.
*A61B 1/06* (2006.01)
*A61B 1/04* (2006.01)
(52) U.S. Cl. .......................... 600/175; 600/178; 600/118
(58) Field of Classification Search .................. 600/175, 600/118, 132, 133, 178, 155, 101, 182, 180, 600/157
See application file for complete search history.

(56) References Cited

U.S. PATENT DOCUMENTS

| | | | | |
|---|---|---|---|---|
| 2,004 A | * | 3/1841 | Ogawa | 440/90 |
| 7,435,218 B2 | * | 10/2008 | Krattiger et al. | 600/175 |
| 7,637,866 B2 | * | 12/2009 | Ono | 600/134 |
| 7,695,431 B2 | * | 4/2010 | Okada | 600/176 |
| 7,850,606 B2 | * | 12/2010 | Yokota | 600/175 |
| 2005/0014996 A1 | * | 1/2005 | Konomura et al. | 600/175 |
| 2005/0159646 A1 | * | 7/2005 | Nordstrom et al. | 600/127 |
| 2007/0100202 A1 | * | 5/2007 | Murata | 600/109 |

FOREIGN PATENT DOCUMENTS

| | | | |
|---|---|---|---|
| JP | 2004-033487 | * | 5/2004 |
| JP | 2006-191990 A | | 7/2006 |
| JP | 2006-212335 A | | 8/2006 |

* cited by examiner

*Primary Examiner* — John P Leubecker
*Assistant Examiner* — Ronald D Colque
(74) *Attorney, Agent, or Firm* — Holtz, Holtz, Goodman & Chick, PC

(57) ABSTRACT

An endoscope apparatus includes: an optical adapter provided with a discrimination capacitor; and an endoscope configured to be detachably provided with the optical adapter at a distal end portion of the endoscope, and configured to include a reference capacitor which is arranged to be connected in series to the discrimination capacitor in a state where the optical adapter is mounted, a DC power supply which is connected in series to the reference capacitor, and a control circuit which calculates a capacitance of the discrimination capacitor on the basis of a voltage value at a connection point between the discrimination capacitor and the reference capacitor, so as to discriminate the kind of the optical adapter.

11 Claims, 5 Drawing Sheets

ENDOSCOPE APPARATUS

This application claims benefit of Japanese Application No. 2007-25983 filed in Japan on Feb. 5, 2007, the contents of which are incorporated by this reference.

BACKGROUND OF THE INVENTION

1. Field of the Invention

The present invention relates to an endoscope apparatus, and more particularly to an endoscope apparatus configured by mounting an optical adapter, having illumination means, at a distal end of an insertion portion of the endoscope apparatus.

2. Description of the Related Art

In recent years, there has been widely used an endoscope apparatus which is capable of observing an organ, and the like, in a body cavity by inserting a thin and long insertion portion into the body cavity, and performing various medical treatment by using a treatment tool inserted in a treatment tool channel as required. Also in the industrial field, industrial endoscope apparatuses have been widely used for observing and inspecting damage, corrosion, and the like, in the inside of a boiler, a turbine, an engine, a chemical plant, and the like.

As the endoscope apparatus used as described above, there is an electronic endoscope apparatus in which an image pickup device, such as a CCD, for photo-electrically converting an optical image into an image signal, is arranged at the distal end portion of the insertion portion. In the electronic endoscope apparatus, observation can be performed by such a way that a video signal is generated in an image processing portion from an image signal of an observation image formed on the image pickup device, and the generated video signal is outputted to a monitor so as to display an endoscopic image on a screen.

Further, in particular, in the industrial endoscope apparatus, a plurality of kinds of optical adapters are prepared so as to enable the observation to be performed in correspondence with inspection points. Also, the optical adapters are configured so as to be able to be detachably mounted to the distal end portion of the insertion portion of the endoscope apparatus as required. In this way, in the endoscope apparatus using the plurality of kinds of optical adapters, specifications of drive, control, and the like, are changed according to the optical adapter, and hence it is important to accurately discriminate the kind of the optical adapter mounted to the endoscope apparatus.

For example, as disclosed in Japanese Patent Laid-Open No. 2006-212335, as the endoscope apparatus provided with exchange type optical adapters, there is proposed, for example, an endoscope apparatus configured in such a manner that an EEPROM storing intrinsic control information corresponding to the kind of each optical adapter is incorporated in the optical adapter, and that when the optical adapter is mounted to the distal end portion of the insertion portion, the endoscope apparatus side reads the control information written in the EEPROM and controls the optical adapter on the basis of the control information.

Further, for example, as disclosed in Japanese Patent Laid-Open No. 2006-191990, there is also proposed an endoscope apparatus configured in such a manner that intrinsic control information corresponding to the kind of each optical adapter is stored in an RFID tag incorporated in the optical adapter, and that when the optical adapter is mounted to the distal end portion of the insertion portion, the endoscope apparatus side reads the control information written in the RFID tag and controls the optical adapter on the basis of the control information.

Further, there is also generally known an endoscope apparatus configured in such a manner that that a resistance of 1Ω, 10 kΩ or the like which can be easily discriminated is mounted in the optical adapter, and that when the optical adapter is mounted to the endoscope apparatus, the kind of the optical adapter is discriminated by measuring a value of the resistance or measuring a voltage divided between the resistance and a reference resistance in the endoscope main body, and thereby the optical adapter is controlled.

SUMMARY OF THE INVENTION

An endoscope apparatus according to an aspect of the present invention is featured by including: an optical adapter which has a first capacitor; and an endoscope which is detachably provided with the optical adapter at a distal end portion of the endoscope, and which includes a second capacitor arranged so as to be connected in series to the first capacitor in a state where the optical adapter is mounted, a DC power supply connected in series to the second capacitor, and a control section configured to calculate a capacitance value of the first capacitor on the basis of a voltage value at a connection point between the first capacitor and the second capacitor, and configured to discriminate the kind of the optical adapter by comparing the capacitance value with a reference value, in the endoscope main body.

DETAILED DESCRIPTION OF THE PREFERRED EMBODIMENTS

In the following, embodiments according to the present invention will be described with reference to the accompanying drawings.

First Embodiment

Figure 1:
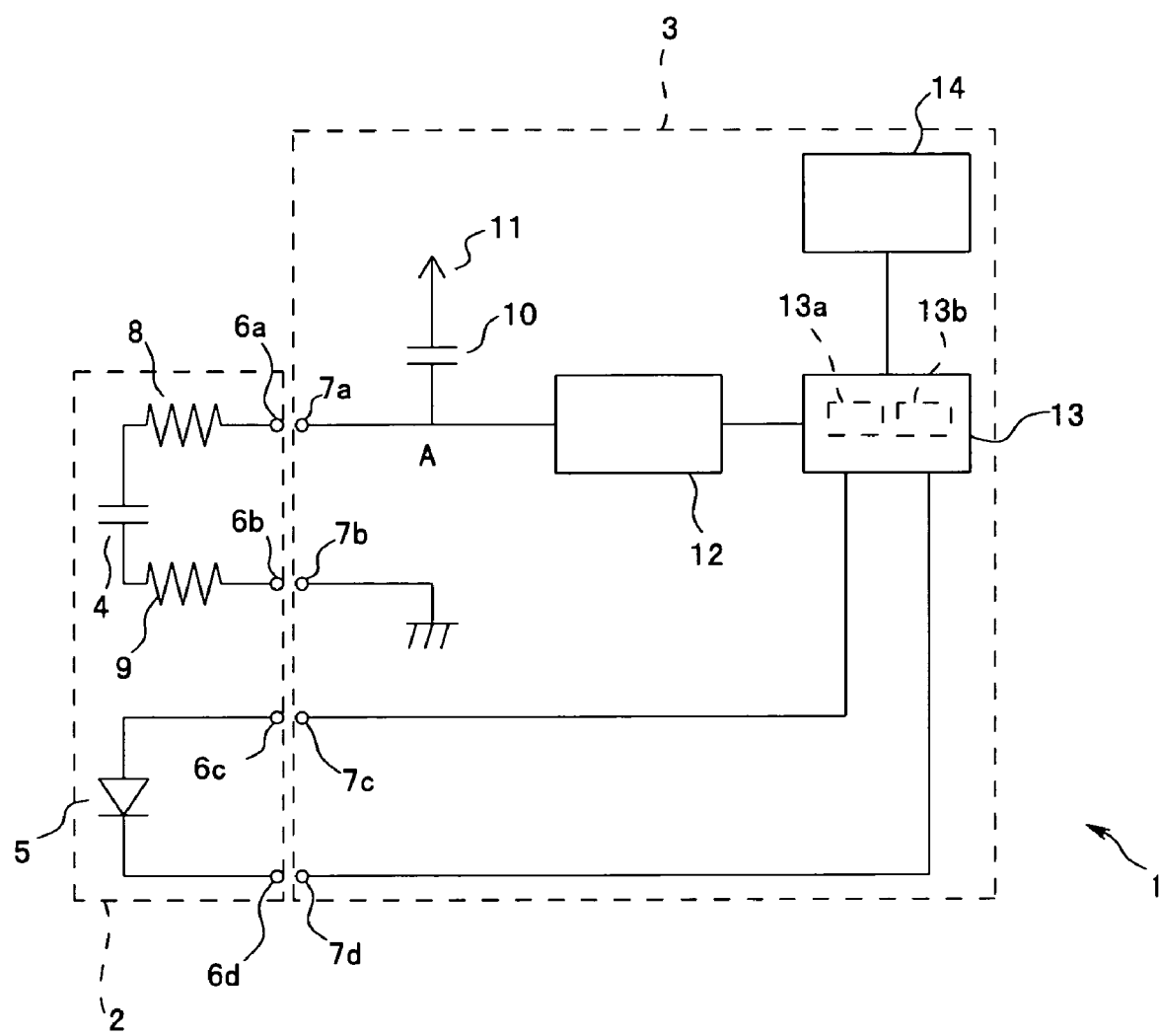
FIG. 1 is a schematic view for explaining a configuration of an endoscope apparatus 1 according to a first embodiment of the present invention.

First, a configuration of an endoscope apparatus 1 according to a first embodiment of the present invention will be described with reference to FIG. 1. FIG. 1 is a schematic view for explaining a configuration of an endoscope apparatus 1 according to a first embodiment of the present invention.

The endoscope apparatus 1 according to the present embodiment includes an optical adapter 2 and an endoscope 3 having a distal end portion to which the optical adapter 2 can be detachably mounted. The optical adapter 2 is mainly configured by a discrimination capacitor 4 as a first capacitor for enabling the kind of the optical adapter 2 to be discriminated on the side of the endoscope 3, an illumination LED 5, an objective optical system and an illumination optical system (both not shown). Further, the optical adapter 2 has connectors 6a to 6d. The optical adapter 2 is mounted to the endoscope 3 by respectively connecting the connectors 6a to 6d to connectors 7a to 7d provided in the endoscope 3.

There exist contact resistances between the connectors 6a to 6d and the connectors 7a to 7d. The contact resistances are not actually mounted in the optical adapter 2 as specific resistances, but here, for convenience of explanation, the contact resistances are illustrated as a contact resistance 8 and a contact resistance 9 in FIG. 1. Note that by the use of the endoscope apparatus, the values of the contact resistances 8 and 9 are changed with time, due to adhesion of fats and oils, rusting, contamination, scraping of contact portions, and the like. That is, the values of the contact resistances 8 and 9 are changed with time.

When the optical adapter 2 is connected to the endoscope 3 by the connectors 6a to 6d and the connectors 7a to 7d, one end of the discrimination capacitor 4 is connected, via the connectors 6a and 7a, to one end of a reference capacitor 10 as a second capacitor which is provided in the endoscope 3. Note that the other end of the reference capacitor 10 is connected to a DC power supply 11 which is also provided in the endoscope 3. Further, the other end of the discrimination capacitor 4 is grounded to GND from the inside of the endoscope 3 via the connectors 6b and 7b.

That is, the reference capacitor 10, the contact resistance 8, the discrimination capacitor 4, and the contact resistance 9 are connected in series between the DC power supply 11 and the GND. Except the transient period when the power supply is turned on, at a connection point A between the reference capacitor 10 and the discrimination capacitor 4, the DC voltage applied by the DC power supply 11 is divided according to the respective capacitances of the reference capacitor 10 and the discrimination capacitor 4. Note that since a DC current does not flow through the capacitors connected in series, the voltage at the connection point A is not influenced by the contact resistances 8 and 9, and is determined only by the capacitance ratio between the discrimination capacitor 4 and the reference capacitor 10.

Further, an AD converter 12 is connected to the connection point A between the discrimination capacitor 4 and the reference capacitor 10. The voltage value at the connection point A, which is a voltage divided by the reference capacitor 10 and the discrimination capacitor 4, is inputted into the AD converter 12 so as to be digitized. The output from the AD converter 12 is inputted into a control circuit 13 as a control section which is also provided in the endoscope 3. The control circuit 13 is configured by including a CPU 13a and a memory 13b. In the control circuit 13, the output from the AD converter 12 (=the digitized voltage divided by the reference capacitor 10 and the discrimination capacitor 4) is compared with a reference value in the endoscope 3, so that the kind of the optical adapter 2 is discriminated. The illumination LED 5 of the optical adapter 2 is also connected to the control circuit 13, which performs control so as to enable a suitable current to flow through the illumination LED 5 depending on the discriminated kind of the optical adapter 2.

For example, in the case where four kinds of optical adapters 2 can be mounted to the endoscope 3, four capacitors having capacitances whose capacitance ratios with respect to the reference capacitor 10 are respectively 1:1, 1:10, 1:100 and an open state value, are mounted in the respective optical adapters 2 as the discrimination capacitor 4. On the other hand, a correspondence relation between a ratio of the voltage value inputted from the AD converter 12 to the value of voltage applied from the DC power supply 11, and the optical adapter 2 is initially set in the control circuit 13 of the endoscope 3.

Figure 2A:
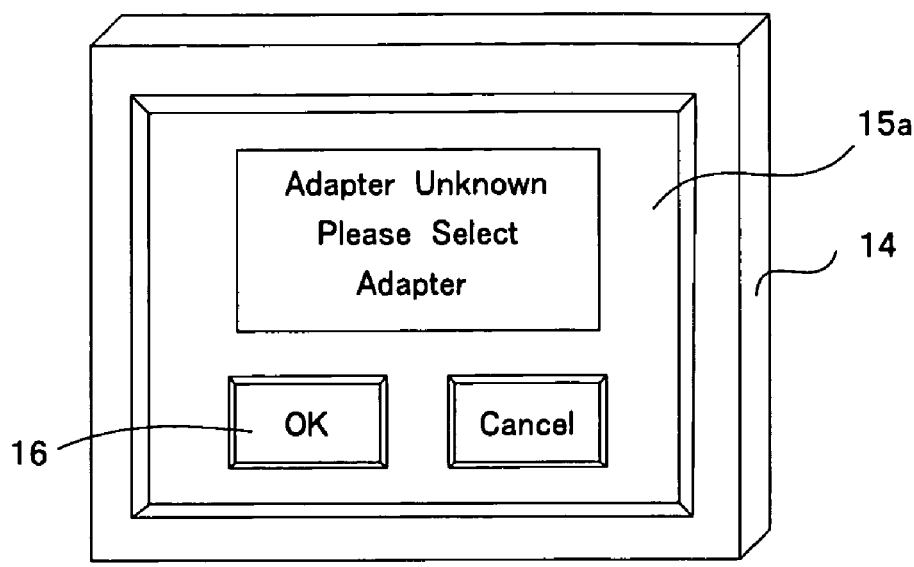
FIG. 2A and FIG. 2B are figures for explaining screen examples of a display device 14 at the time of initially setting an optical adapter 2 mounted to an endoscope 3.
Figure 2B:
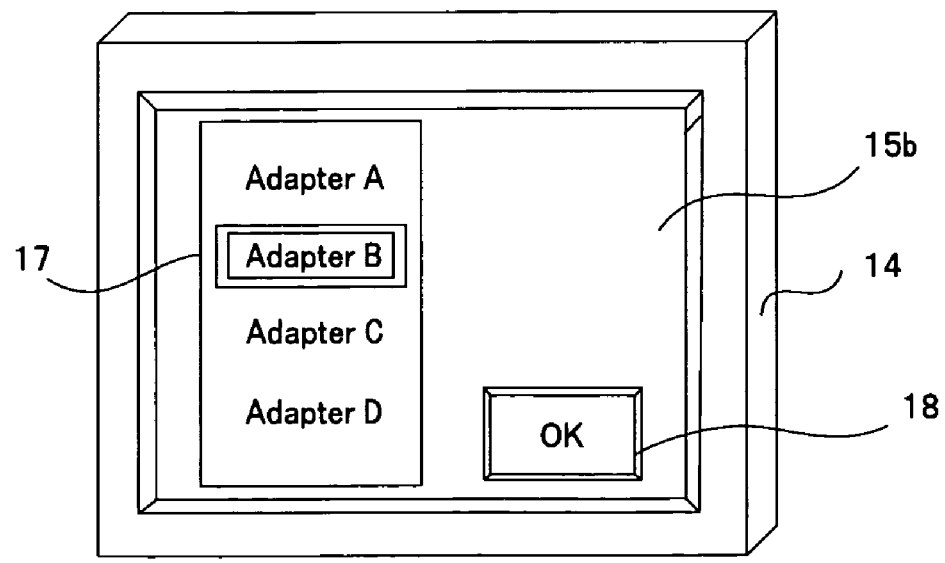

For example, the initial setting is performed as follows. First, in a state where the correspondence relation is not set in the control circuit 13, when the optical adapter 2 is mounted to the endoscope 3, a screen 15a as shown in FIG. 2A is displayed in a display device 14. FIG. 2A and FIG. 2B are figures for explaining screen examples of the display device 14 at the time of initially setting the optical adapter 2 mounted to the endoscope 3. When a user selects an OK button 16 by using the screen 15a of the display device 14, an operation panel (not shown), or the like, a screen 15b as shown in FIG. 2B is displayed in the display device 14. When the user selects Adapter B from four options displayed in an adapter list 17 and subsequently selects an OK button 18 by using the screen 15b of the display device 14, the operation panel (not shown), or the like, the optical adapter 2 which is mounted at that time is set as Adapter B in the control circuit 13.

For example, the optical adapters 2 provided with the discrimination capacitors 4 having capacitances whose capacitance ratios with respect to the reference capacitor 10 are respectively 1:1, 1:10, 1:100, and the open state value, are initially set as Adapters A, B, C and D, respectively. Then, when the endoscope apparatus 1 is used, and when the voltage value at the connection point A is 9/10 of the value of voltage applied from the DC power supply 11, the control circuit 13 determines that the Adapter B, that is, the optical adapter 2 having the discrimination capacitor 4 whose capacitance ratio with respect to the reference capacitor 10 is 1:10, is connected to the endoscope 3.

Further, the control circuit 13 determines a value of current according to the number of illumination LEDs 5 mounted in the optical adapter 2, and performs control so as to enable the current to actually flow through the illumination LEDs 5. Further, the control circuit 13 performs control of various processing corresponding to the kind of the mounted optical adapter 2, processing independent of the kind of the optical adapter 2, and the like.

Further, the display device 14 provided in the endoscope 3 is connected to the control circuit 13. In the display device 14, there are displayed an image picked up by an image pickup device (not shown) provided in the endoscope 3, the results of various processing controlled by the control circuit 13, and the like.

Note that the voltage value at the connection point A is not influenced by the values of the contact resistances 8 and 9. However, when the values of the contact resistances 8 and 9 are significantly changed due to adhesion of fats and oils, rusting, contamination, scraping of contact portions, and the like, the time required for determining the voltage value at the connection point A is increased. Since the kind of the optical adapter 2 needs to be discriminated in a limited short time, the control circuit 13 is made to measure the divided voltage in such a transient state.

Figure 3A:
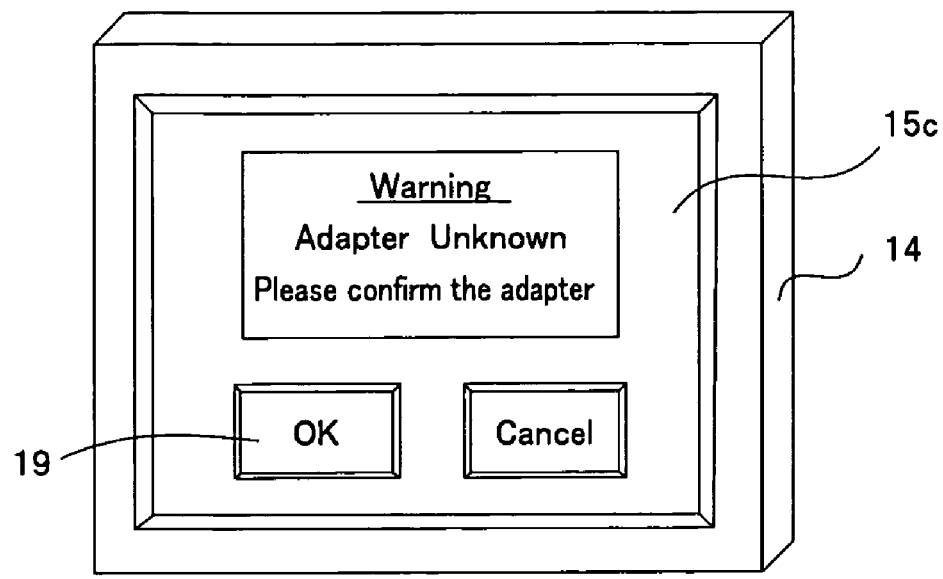
FIG. 3A and FIG. 3B are figures for explaining screen examples of the display device 14 at the time of resetting the optical adapter 2 mounted to the endoscope 3.
Figure 3B:
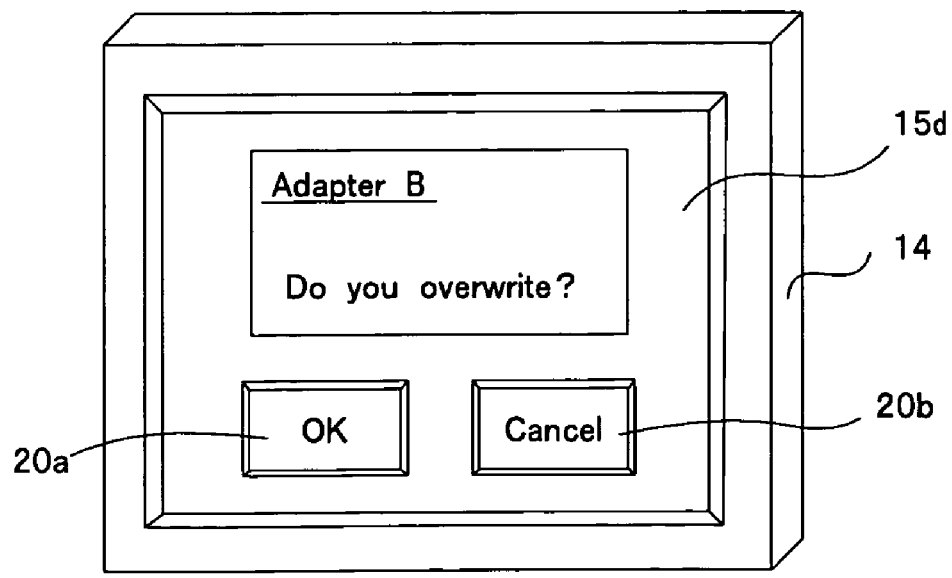

In this case, it is difficult to maintain the measuring accuracy, and the kind of the optical adapter 2 may be erroneously recognized in some cases. Therefore, for example, when a value beyond ±20% of the voltage value used as the discrimination reference is inputted into the control circuit 13, the optical adapter 2 is not automatically discriminated, but a warning screen 15c, for example, as shown in FIG. 3A is displayed in the display device 14, so as to enable the user to manually select the kind of the optical adapter 2, or to reset the kind of the optical adapter 2 to make the kind of the optical adapter 2 correspond to the detected voltage value. FIG. 3A and FIG. 3B are figures for explaining screen examples of the display device 14 at the time of resetting the optical adapter 2 mounted to the endoscope 3. The processing relating to FIG. 3A and FIG. 3B, and the processing shown in FIG. 4 as will be described below, configures a reference value setting portion which, when the measured divided voltage value is not within a predetermined set range, changes a reference value of the set range.

When the user selects an OK button 19 by using a screen 15c of the display device 14 or an operation panel (not shown), a screen 15d as shown in FIG. 3B is displayed in the display device 14. When the user selects an OK button 20a, a voltage value at that time is overwritten on the voltage value used as the discrimination reference of Adapter B in the control circuit 13. Further, when a cancel button 20b is selected, after the contact points between the optical adapter 2 and the endoscope 3 are cleaned, the voltage value at the connection point A is measured again. When the voltage value at the connection point A becomes more or less than ±20% of the voltage value as the discrimination reference even after the contacts are cleaned, the warning screen 15c is again displayed as shown in FIG. 3A. In this way, when the user selects and inputs the kind of the optical adapter 2 according to the warning display, the control circuit 13 performs various control according to the inputted kind of the optical adapter 2.

Figure 4:
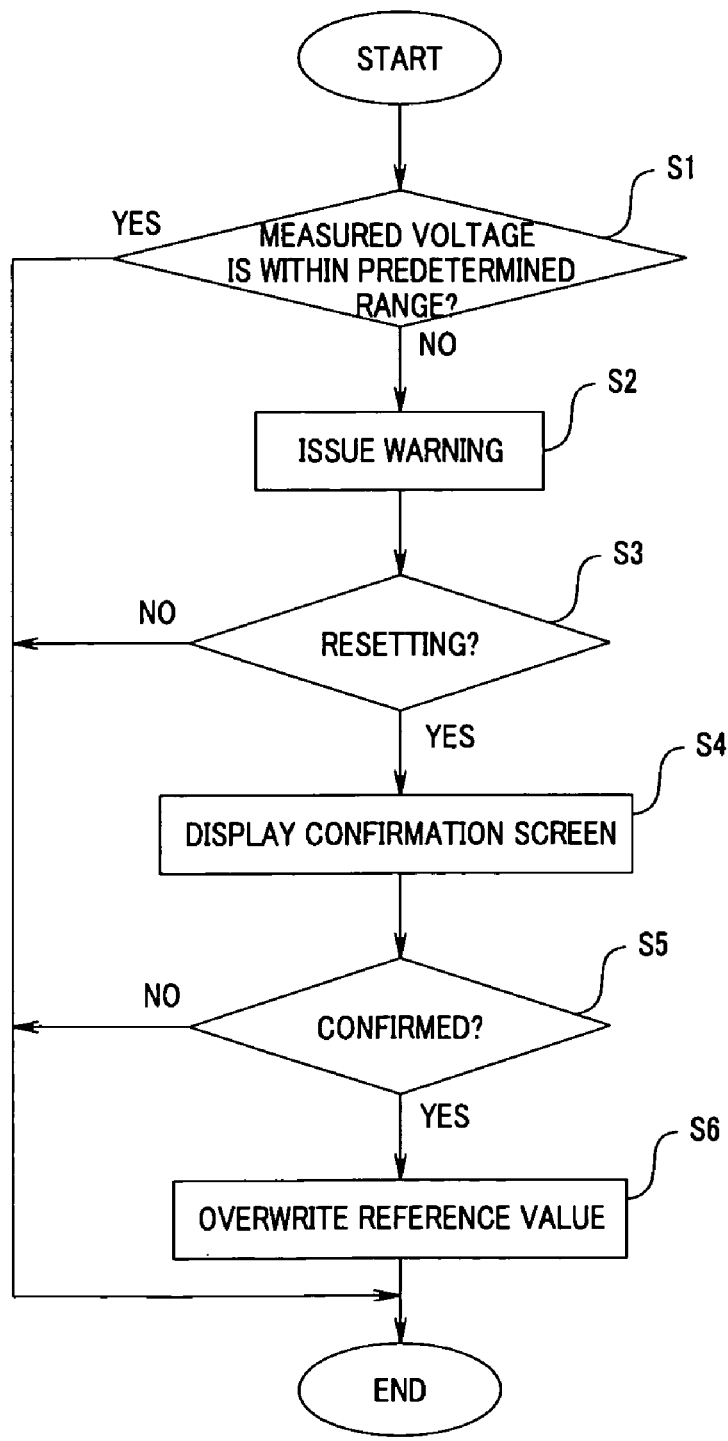
FIG. 4 is a flow chart showing an example of a flow of reset processing of a voltage value used as a reference of discrimination performed in a control circuit.

The above described processing is performed in the control circuit 13 including the CPU 13a, the memory 13b, and the like. FIG. 4 is a flow chart showing an example of a flow of reset processing of a voltage value used as a reference of discrimination performed in the control circuit.

First, the control circuit 13 determines whether or not a measured voltage value is within a predetermined range with respect to the voltage value used as the discrimination reference (step S1).

When the measured voltage value is within the predetermined range with respect to the voltage value used as the discrimination reference, the determination result is YES in step S1, and the processing is ended.

When the measured voltage value is not within the predetermined range with respect to the voltage value used as the discrimination reference, the determination result is NO in step S1, the warning display by the warning screen 15c as shown in FIG. 3A is performed on the display device 14 (step S2).

Then, the control circuit 13 determines whether or not the OK button 19 is selected in screen 15c, that is, whether or not an instruction to reset the discrimination reference value is given (step S3). That is, the user instructs to set the discrimination reference value by selecting the OK button 19.

When NO in step S3, that is, when the resetting of the discrimination reference value is not performed, the control circuit 13 performs no processing and ends the processing.

When YES in step S3, that is, when the resetting of the discrimination reference value is performed, the control circuit 13 displays the reset confirmation screen 15d of FIG. 3B on the display device 14 (step S4). The screen 15d is a screen to urge the user to instruct to set the discrimination reference value.

The control circuit 13 determines whether or not the OK button 20a is selected on the screen 15d, that is, whether or not an instruction to overwrite the discrimination reference value in the memory 13b with a new value is given (step S5). That is, the user confirms the instruction to set the discrimination reference value by selecting the OK button 20a.

When NO in step S5, that is, when the overwriting of the discrimination reference value is not performed, the control circuit 13 performs no processing and ends the processing.

When YES in step S5, the instruction to set the discrimination reference value is confirmed by the user, and hence the control circuit 13 overwrites, that is, update the data of the discrimination reference value in the memory 13b with the measured voltage value (step S6).

In this way, in the present embodiment, instead of an impedance element such as a resistance, the discrimination capacitor 4 is mounted in the optical adapter 2 so as to be connected in series to the reference capacitor 10 in the endoscope 3, and the optical adapter 2 is discriminated by detecting a divided voltage at the connection point A. Since the divided voltage is not influenced by the contact resistances 8 and 9 between the optical adapter 2 and the endoscope 3, it is possible to surely discriminate the kind of the optical adapter 2.

Further, when the values of the contact resistances 8 and 9 are increased, and when the kind of the optical adapter may be erroneously recognized because time is required until the divided voltage is converged to a constant value, the user is enabled to select the kind of the optical adapter 2, and thereby improper use of the optical adapter 2 can be prevented. Further, by manually selecting a suitable kind of the optical adapter, the user is able to perform more suitable control as compared with the control based on automatic discrimination information with low accuracy, and thereby is able to easily perform observation with suitable light quantity.

Further, the kind of the optical adapter 2 is discriminated by the ratio between the discrimination capacitor 4 and the reference capacitor 10. Thus, even when the kind of the optical adapters 2 to be mounted to the endoscope 3 is increased, suitable discrimination information can be obtained only by providing the four connectors 6a to 6d in the optical adapter 2, and providing the four connectors 7a to 7d in the endoscope 3. Thereby, it is possible to prevent to increase the size of the endoscope apparatus.

Note that in the present embodiment, the connectors 6c, 6d, 7c and 7d are required because of the need to flow a current through the illumination LED provided in the optical adapter, but only connectors 6a, 6b, 7a and 7b are required only for the purpose of discriminating the kind of the optical adapter.

Note that the present embodiment is configured such that when the values of the contact resistances 8 and 9 are increased, and when the kind of the optical adapter 2 may be erroneously recognized, the screen to urge the kind of the optical adapter to be manually input is displayed on the display device 14. However, it is only necessary to stop the automatic discrimination by the control circuit 13, and to switch from the automatic discrimination to the manual selection. For example, a screen may also be displayed to urge the optical adapter 2 to be exchanged.

Second Embodiment

Figure 5:
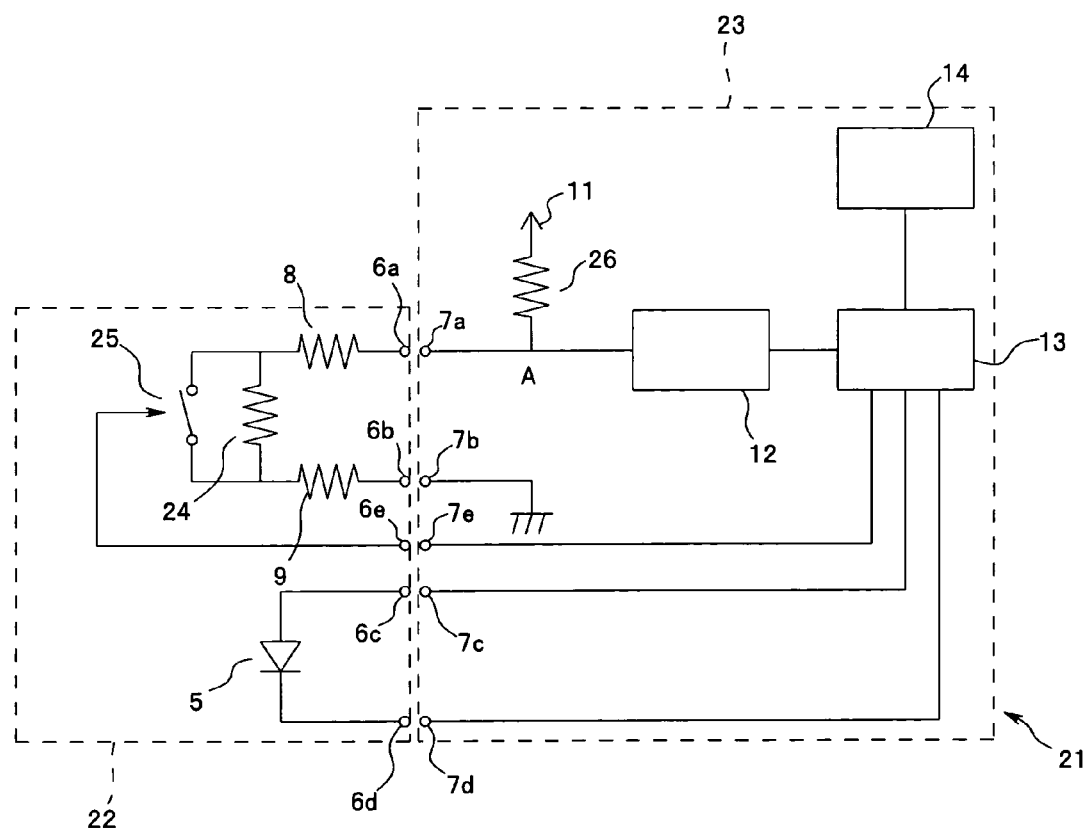
FIG. 5 is a schematic view for explaining a configuration of an endoscope apparatus 21 according to a second embodiment of the present invention.

Next, an endoscope apparatus according to a second embodiment of the present invention will be described with reference to FIG. 5. FIG. 5 is a schematic view for explaining a configuration of an endoscope apparatus 21 according to a second embodiment of the present invention. The configuration of the endoscope apparatus 21 according to the present embodiment is the same as that of the endoscope apparatus 1 of the first embodiment as described with reference to FIG. 1, except that the capacitors for discriminating the kind of the optical adapter are replaced by impedance elements (resistances) and a switch element. Thus, the same components are denoted by the same reference numerals and characters, and the explanation thereof is omitted.

An optical adapter 22 which configures the endoscope apparatus 21 according to the present embodiment, is mainly configured by a discrimination resistance 24 as a first resistance for discriminating the kind of the optical adapter 22 on the side of an endoscope 23, a switch element 25, an illumination LED 5, an objective optical system and an illumination optical system (both not shown). Further, the optical adapter 22 includes connectors 6a to 6e. The discrimination resistance 24 and the switch element 25 are connected in parallel with each other between the connectors 6a and 6b. The connectors 6a to 6e and connectors 7a to 7e provided in the endoscope 23 are respectively connected to each other, and thereby the optical adapter 22 is mounted to the endoscope 23.

When the optical adapter 22 and the endoscope 23 are connected to each other by the connectors 6a to 6e and the connectors 7a to 7e, one end of the discrimination resistance 24 and the switch element 25 is connected to one end of a reference resistance 26 as a second resistance provided in the endoscope 23 via the connectors 6a and 7a. Further, a control terminal of the switch element 25 is connected to a control circuit 13 in the endoscope 23 via the connectors 6e and 7e. Note that the other terminal of the reference resistance 26 is connected to a DC power supply 11 similarly provided in the endoscope 23. Further, the other one end of the discrimination resistance 24 and the switch element 25 is grounded to the GND from the inside of the endoscope 23 via the connectors 6b and 7b.

Next, a method for discriminating the optical adapter 22 will be described in conjunction with the endoscope apparatus 21 in the present embodiment.

First, when the optical adapter 22 is mounted to the endoscope 23, the switch element 25 is closed according to a control signal from the control circuit 13. In this state, a voltage value Va at a connection point A is measured so as to be digitized by an AD converter 12, and is then inputted into the control circuit 13. Here, the voltage value Va is a voltage divided according to the ratio of the reference resistance 26 to a combined resistance of the contact resistances 8 and 9 which are connected in series to each other. The endoscope 23 has the information on the optical adapter 22, defined beforehand in correspondence with the voltage value Va, so that a suitable optical adapter 22 is selected. Note that the method for initially setting the information about the optical adapter 22 in the control circuit 13 of the endoscope 23 can be performed similarly to the first embodiment as described with reference to FIG. 2A and FIG. 2B.

Then, according to the control signal from the control circuit 13, the switch element 25 is opened. In this state, a voltage value Vb at the connection point A is measured, so as to be digitized by the AD converter 12, and is then inputted into the control circuit 13. Here, the voltage value Vb is a voltage divided according to the ratio of the reference resistance 26 to a combined resistance of a contact resistance 8, the discrimination resistance 24, and a contact resistance 9 which are connected in series.

In the control circuit 13, when both the voltage value Va and the voltage value Vb are inputted, a value of the discrimination resistance 24 is calculated by using these values and the value of the reference resistance 26.

For example, when four kinds of optical adapters 22 can be mounted to the endoscopes 23, four kinds of resistances of 1 kΩ, 10 kΩ, 100 kΩ, and an open state value are mounted in the respective optical adapters 22 as the discrimination resistance 24. When the value of the discrimination resistance 24 calculated by the above described discrimination method is not less than 800Ω and less than 2 kΩ, the control circuit 13 recognizes the value of the discrimination resistance 24 as 1 kΩ, and determines that the optical adapter 22 having the discrimination resistance 24 of 1 kΩ is connected to the endoscope 23.

Similarly, when the value of the discrimination resistance 24 calculated by the above described discrimination method is in a range from not less than 8 kΩ to less than 20 kΩ, a range from not less than 80 kΩ to less than 200 kΩ, and a range not less than 800 kΩ, the control circuit 13 respectively recognizes the value of the discrimination resistance 24 as 10 kΩ, 100 kΩ, and the open state value, and determines that the optical adapter 22 having each of the resistance values is connected to the endoscope 23.

Note that when the values of the contact resistances 8 and 9 are significantly changed due to adhesion of fats and oils, rusting, contamination, scraping of contact portions, and the like, the calculation accuracy of the discrimination resistance 24 is deteriorated, and thereby the kind of the optical adapter 22 may be erroneously recognized in some cases. For this reason, when the value of the discrimination resistance 24 calculated by the above described discrimination method is in one of a range from not less than 0Ω to less than 800Ω, a range from not less than 2 kΩ to less than 8 kΩ, a range from not less than 20 kΩ to less than 80 kΩ and a range from not less than 200 kΩ to less than 800 kΩ, the kind of the optical adapter 22 is not automatically discriminated, but a warning is displayed in a display device 14 similarly to the endoscope apparatus 1 of the first embodiment as described with reference to FIG. 3A, FIG. 3B and FIG. 4, so as to enable the user to manually select the kind of the optical adapter 22, or to reset the kind of the optical adapter 22 in correspondence with the combined resistance. When the user selects and inputs the kind of the optical adapter 22 according to the warning display, the control circuit 13 performs various control according to the kind of the optical adapter 22 which has been inputted.

In this way, according to the present embodiment, in the state where the discrimination resistance 24 and the switch element 25 are connected in parallel to each other, so as to be mounted in the optical adapter 2, and are also connected in series to the reference resistance 26 in the endoscope 23, the optical adapter 22 is discriminated by using the divided voltage VA at the connection point A at the time when the switch element is closed, the divided voltage VB at the connection point A at the time when the switch element is opened, and the value of the reference resistance 26. Thereby, the influence of the contact resistances 8 and 9 between the optical adapter 22 and the endoscope 23 can be eliminated, and hence the kind of the optical adapter 22 can be surely discriminated.

Further, it is configured such that, when the values of the contact resistances 8 and 9 are increased so as to deteriorate the calculation accuracy of the discrimination resistance 24 and thereby the kind of the optical adapter 22 may be erroneously recognized, the user is made to select the kind of the optical adapter 22. As a result, it is possible to prevent to erroneously use the optical adapter 22.

Note that in the present embodiment, visual means for displaying the warning message in the display device 14, such as an LCD and a CRT, is used. However, audible means based on a voice, a buzzer, or the like, may also be used. Further, even when the similar visual means is used, the warning message may also be displayed in a part of an icon, the operation panel, the operation portion, the endoscope 23 main body, and the like. Alternatively, an LED may also be turned on.

As described above, according to each of the above described embodiments, in the case where an element, such as a resistance, which can be easily mounted in order to discriminate the kind of the optical adapter, is used, it is possible to surely discriminate the kind of the optical adapter, even when the contact resistance between the optical adapter and the distal end portion is significantly changed. Further, even when the measurement error is increased, and when the kind of the optical adapter may be erroneously recognized, it is possible to prevent improper use of the optical adapter.

Having described the embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:
    an optical adapter including a first resistance and a switch element which are connected in parallel to each other;
    an endoscope comprising a distal end portion to which the optical adapter is detachably mountable;
    a second resistance which is arranged to be connected in series to the first resistance when the optical adapter is mounted to the distal end portion of the endoscope;
    a DC power supply which is connected in series to the second resistance; and
    a control section which calculates a value of the first resistance based on (i) a first divided voltage value at a connection point between the first resistance and the second resistance at a time when the switch element is closed, (ii) a second divided voltage value at the connection point at a time when the switch element is opened, and (iii) a value of the second resistance, wherein the control section discriminates a kind of the optical adapter based on the calculated value of the first resistance.

2. The endoscope apparatus according to claim 1, wherein when the value of the first resistance calculated by the control section is not included in a predetermined set range, the control section stops the discrimination of the kind of the optical adapter.

3. The endoscope apparatus according to claim 2, wherein the endoscope comprises a warning section configured to warn that the value of the first resistance calculated by the control section is not included in the predetermined set range.

4. The endoscope apparatus according to claim 3, wherein the endoscope further comprises a display portion which displays an alarm when the value of the first resistance calculated by the control section is not included in the predetermined set range.

5. The endoscope apparatus according to claim 4, wherein when the value of the first resistance calculated by the control section is not included in the predetermined set range, the kind of the optical adapter can be set manually.

6. An endoscope apparatus configured to discriminate a kind of an optical adapter which can be detachably mounted to a distal end portion of an endoscope, wherein the optical adapter includes a first resistance and a switch element which are connected in parallel, and the endoscope includes a second resistance that is connected in series to the first resistance when the optical adapter is mounted to the distal end portion of the endoscope, the endoscope apparatus comprising:
    a control section configured to calculate a value of the first resistance in the optical adapter and to discriminate the kind of the optical adapter based on the calculated value of the first resistance, wherein the control section is configured to calculate the value of the first resistance based on (i) a first divided voltage value at a connection point between the first resistance and the second resistance at a time when the switch element is closed, (ii) a second divided voltage value at the connection point at a time when the switch element is opened, and (iii) a value of the second resistance; and
    a warning section which is configured to warn that the calculated value of the first resistance is not within a predetermined set range, when the calculated value of the first resistance is not within the predetermined set range.

7. The endoscope apparatus according to claim 6, wherein the warning section warns via a warning display on a screen of a display device.

8. The endoscope apparatus according to claim 6, further comprising a reference value setting portion which changes a reference value of the predetermined set range.

9. The endoscope apparatus according to claim 8, wherein the reference value setting portion changes the reference value in response to an instruction input using a screen of a display device, when the calculated value of the first resistance is not within the predetermined set range.

10. The endoscope apparatus according to claim 8, further comprising a memory for storing the reference value, wherein the reference value setting portion changes the reference value in the memory based on the calculated value of the first resistance.

11. The endoscope apparatus according to claim 10, wherein the warning section warns via a warning display on a screen of a display device, and
    wherein the reference value setting portion overwrites the reference value in the memory after a setting instruction to change the reference value is confirmed on the screen.

* * * * *